United States Patent
Havel et al.

(10) Patent No.: US 6,546,287 B1
(45) Date of Patent: Apr. 8, 2003

(54) CONTROLLED-POWER DEFIBRILLATOR AND METHOD OF DEFIBRILLATION

(75) Inventors: William J. Havel, Maple Grove, MN (US); Joe D. Bourland, West Lafayette, IN (US); Leslie A. Geddes, Lafayette, IN (US); Willis A. Tacker, Lafayette, IN (US); Darrell O. Wagner, Isanti, MN (US)

(73) Assignee: Purdue Research Foundation, West Lafayette, IN (US)

( * ) Notice: Subject to any disclaimer, the term of this patent is extended or adjusted under 35 U.S.C. 154(b) by 279 days.

(21) Appl. No.: 09/680,790

(22) Filed: Oct. 6, 2000

Related U.S. Application Data (60) Provisional application No. 60/158,498, filed on Oct. 8, 1999.

(51) Int. Cl.⁷ .................................................. A61N 1/36
(52) U.S. Cl. ................................................ 607/7; 607/8
(58) Field of Search .............................. 607/5, 7, 8, 62, 607/68, 72, 74

(56) References Cited

U.S. PATENT DOCUMENTS

| | | | | |
|---|---|---|---|---|
| 3,886,950 A | * | 6/1975 | Ukkestad ........................ 607/8 |
| 4,328,808 A | | 5/1982 | Charbonnier et al. ........ 128/419 |
| 4,574,810 A | | 3/1986 | Lerman ........................ 128/419 |
| 4,821,723 A | | 4/1989 | Baker, Jr. et al. ........ 128/419 D |
| 4,840,177 A | | 6/1989 | Charbonnier et al. ........ 128/419 |
| 5,088,489 A | | 2/1992 | Lerman ........................ 128/419 |
| 5,111,813 A | | 5/1992 | Charbonnier et al. ........ 128/419 |
| 5,593,427 A | | 1/1997 | Gliner et al. ..................... 607/7 |
| 5,607,454 A | | 3/1997 | Cameron et al. ............... 607/5 |
| 5,650,750 A | | 7/1997 | Leyde et al. ..................... 330/2 |
| 5,725,560 A | | 3/1998 | Brink .............................. 607/5 |
| 5,733,310 A | | 3/1998 | Lopin et al. ..................... 607/7 |
| 5,749,904 A | | 5/1998 | Gliner et al. ..................... 607/7 |
| 5,800,463 A | | 9/1998 | Lopin et al. ..................... 607/8 |
| 5,836,978 A | | 11/1998 | Gliner et al. ..................... 607/7 |
| 5,999,852 A | | 12/1999 | Elabbady et al. ............... 607/8 |
| 6,047,212 A | | 4/2000 | Gliner et al. ..................... 607/7 |

OTHER PUBLICATIONS

Geddes, L.A.; Tacker, W.A.; Cabler, P.; Chapman, R.; Rivera, R.; Kidder, H., "The Decrease in Transthoracic Impedance During Successive Ventricular Defibrillation Trials," *Medical Instrumentation*, vol. 9, pp. 179–180, 1975.

Geddes, Leslie A.; Tacker, W.A.; Schoenlein, W.; Minton, M.; Grubbs, S., and Wilcox, P., "The Prediction of the Impedance of the Thorax to Defibrillating Current," *Medical Instrumentation*, vol. 10, pp. 159–162, 1976.

(List continued on next page.)

*Primary Examiner*—Thomas N. Moulis
(74) *Attorney, Agent, or Firm*—William F. Bahret (57) ABSTRACT

A controlled-power defibrillator and method of defibrillation for automatically compensating for changes in patient resistance during delivery of a defibrillation pulse. A switching power converter is connected between a storage capacitor and a pair of electrodes adapted for connection to a patient's body, either internally or externally. A closed-loop power control circuit is operatively connected to the power converter for control of the power delivered to the patient, the power control circuit generating a target voltage signal for the storage capacitor, the target voltage signal having a defined relationship with the waveform of the power desired to be delivered to the patient. The power control circuit monitors the actual voltage on the storage capacitor and adjusts the delivery of power to the patient as a function of the difference between desired and actual storage capacitor voltage. The power converter is adapted to capture energy from the discharge of an existing defibrillator and to convert captured energy from the existing defibrillator to a waveform different from that generated by the existing defibrillator.

24 Claims, 7 Drawing Sheets

OTHER PUBLICATIONS

Sweeney, R.J.; Gill, R.M.; Jones, J.L.; and Reid, P.R., "Defibrillation Using a High–Frequency Series of Monophasic Rectangular Pulses: Observations and Model Predictions," *J. Cardiovasc, Electrophys*, vol. 7, pp. 134–143, 1996.

Geddes, Leslie A.; Havel, William, "Evolution of the Optimum Bidirectional (± Biphasic) Wave for Defibrillation", *Biomedical Instrumentation & Technology*, vol. 34, pp. 39–54, Jan./Feb. 2000.

* cited by examiner

CONTROLLED-POWER DEFIBRILLATOR AND METHOD OF DEFIBRILLATION

CROSS-REFERENCE TO RELATED APPLICATION

The present application claims the benefit of U.S. Provisional Application Ser. No. 60/158,498, filed on Oct. 8, 1999, which is hereby incorporated by reference herein in its entirety.

BACKGROUND OF THE INVENTION

This invention relates to defibrillators and, more particularly, to defibrillators capable of compensating for patient resistance.

Most conventional defibrillators work on the principle of charging a capacitor to a predetermined voltage that corresponds to a desired energy level, and then discharging the capacitor through electrodes into the patient. Since the energy stored in the capacitor is proportional to the square of the capacitor voltage, the energy available to be delivered can be easily controlled in this manner Shaping the waveform is currently accomplished by one of two methods. In the case of the damped sine wave (DSW) defibrillator, an inductor is placed between the capacitor and the electrodes, which creates a damped RLC circuit when connected to a patient and generates a damped sine wave. The base frequency and damping factor can be changed by changing the capacitor or inductance value and are also dependent on the resistance of the patient. In the case of the truncated exponential defibrillator, the time constant of decay of the waveform is adjusted by adjusting capacitor values and is also affected by patient resistance. The waveform can also be temporally shaped through the selected time of truncation. Additionally, the polarity of the connection between capacitor and patient can be reversed during delivery of the waveform to generate a biphasic, bidirectional waveform.

Variability of patient transthoracic resistance presents a problem in the design of defibrillator waveforms. Changes in patient resistance can affect many of the waveform parameters, including waveform size, shape and duration, and as a result can alter the efficacy of the delivered shocks. As a result, defibrillator manufacturers have developed methods for compensating for patient resistance. The notion of designing a defibrillator that is less affected by patient resistance becomes especially important when considering the use of defibrillators out of the hospital in less controlled environments. With the advent of public access defibrillation, a larger percentage of defibrillators will operate out of the hospital. In particular, a recent area of focus in the defibrillation industry has been the automatic external defibrillator (AED). The AED functions like an implantable defibrillator in that it automatically identifies fibrillation and then delivers corrective therapy. The device allows non-medical professionals to resuscitate ventricular fibrillation victims. In such a setting, where it may be impossible for the operator to even estimate an individual's transthoracic resistance, it would naturally be desirable to have a defibrillator that is capable of delivering an effective amount of energy to any individual in a population with a wide range of resistances.

A basic approach to delivering a desired current to a patient is to determine the patient resistance and then deliver a shock with a peak voltage that corresponds to the desired current according to Ohm's law. One such method involves measurement of the subject resistance, before delivering the shock, by passing a low-intensity, high frequency current through the defibrillation electrodes on the subject. This was demonstrated by Geddes et al. as reported in a paper entitled "The Prediction of the Impedance of the Thorax to Defibrillating Current," *Medical Instrumentation*, vol. 10, pp. 159–162, 1976. A limitation of this method is that the patient resistance changes with successive shocks and is also affected by the intensity of the shock. Thus, this method gives only an estimate of the electrode resistance at the time of the delivered shock. Several patents have been issued that relate to this method:

| Pat. No. | Inventor | Issue Date |
| --- | --- | --- |
| 4,574,810 | Lerman | 1986 |
| 4,840,177 | Charbonnier et al. | 1989 |
| 5,088,489 | Lerman | 1992 |
| 5,111,813 | Charbonnier et al. | 1992 |

A technique requiring pre-shock measurement of patient resistance is suggested in U.S. Pat. No. 5,725,560 to Brink for use in scaling a reference waveform having the shape desired for the defibrillation waveform applied to the patient. Brink notes that the defibrillation waveform can be characterized in terms of voltage, current, instantaneous power, or total energy. A closed-loop technique is described with emphasis on current control.

Another method involves delivery of a first shock and measurement of resistance during the shock. The resistance can be determined by measuring delivered voltage and current and using Ohm's law, or it can be determined through the measurement of the RC time constant in the case of a truncated exponential defibrillator where the capacitance C of the defibrillator is known. An example of this method is disclosed in U.S. Pat. No. 4,328,808 to Charbonnier et al. The disclosed device measures peak current and peak voltage and computes resistance using Ohm's law. U.S. Pat. No. 5,733,310 to Lopin et al. describes a method of determining resistance from a shock that is well below threshold levels. The resistance value is used to determine how high to charge the defibrillator capacitance for the subsequent therapeutic shock. Determining resistance from a prior shock involves delivering an extra shock and thus is undesirable. It also can be inaccurate. Geddes et al. have shown that transthoracic resistance decreases with successive defibrillation shocks, which suggests that the resistance measured during the pre-therapy shock may be different than the resistance during therapy. Geddes et al., "The decrease in transthoracic impedance during successive ventricular defibrillation trials," *Medical Instrumentation*, vol. 9, pp. 179–180, 1975.

An additional method for compensating for subject resistance, applicable to truncated exponential defibrillators, uses a fixed tilt waveform. Waveform tilt is defined as the amount the voltage decays between the start and truncation of the waveform:

$$tilt = \frac{V_i - V_f}{V_i}$$

where $V_i$ is the initial voltage of the waveform and $V_f$ is the final voltage. With fixed-tilt waveforms, the voltage on the storage capacitor of the defibrillator is monitored during the delivery of the shock. The shock is terminated when this measured voltage reaches a pre-set value. Thus the storage capacitor always discharges the same amount of energy independent of the patient resistance. Variations of the fixed-tilt method can be found in both implanted and external truncated exponential defibrillators. For example, U.S. Pat. No. 5,593,427 to Gliner et al. suggests the use of fixed tilt with an upper or lower limit on pulse duration. The disadvantage of the fixed-tilt method is that duration is variable and thus cannot be optimized.

Another problem with conventional defibrillators is that fundamental changes to the waveform shape cannot be made. For example, conventional damped sine wave defibrillators cannot be adjusted to deliver a truncated exponential waveform. A biphasic, bidirectional truncated exponential waveform has been shown to have advantages over a damped sine wave, including defibrillation with less energy and fewer electrophysiologic side effects. DSW defibrillators are the prevalent type of defibrillator in use in hospitals today, and they may soon become obsolete due to the improved waveform mentioned above. Therefore, a need exists for a way to adapt existing defibrillators for use in defibrillation with such a new waveform or others.

SUMMARY OF THE INVENTION

The present invention provides, as a first aspect thereof, a controlled-power defibrillator for automatically compensating for changes in patient resistance during delivery of a defibrillation pulse. The controlled-power defibrillator comprises an energy storage device, a pair of electrodes adapted for connection to a patient's body, a power converter having an input connected to the energy storage device and an output connected to the electrodes, and a closed-loop power control circuit operatively connected to the power converter for controlling the power delivered to the patient. The power control circuit includes means for generating a control signal having a defined relationship with a desired delivered power waveform, means for monitoring a parameter having a defined relationship with actual delivered power, and means for adjusting the delivery of power to the patient as a function of the difference between desired power and actual power.

This permits delivery of a waveform having a desired shape, duration and total delivered energy independent of patient resistance, unlike known fixed-tilt methods and others. In its preferred embodiment, the defibrillator controls power by controlling the rate of decay of the voltage on a storage capacitor, which is the preferred form of energy storage device. The control circuit generates a desired capacitor voltage signal as a control signal for this purpose. This desired voltage signal is not the same as the voltage desired to be applied to the patient but has a defined relationship with the desired power waveform delivered to the patient.

According to another aspect of the present invention, a waveform adapter is provided for use with an existing defibrillator capable of generating a given waveform. The waveform adapter is capable of capturing energy from the discharge of the existing defibrillator, converting captured energy to a second waveform and delivering converted energy through a pair of electrodes to a patient.

It is a general object of the present invention to provide improved methods and apparatus for defibrillation.

Another object is to provide a method of defibrillation that is less affected by transthoracic resistance variability than known fixed-tilt methods and other conventional methods of defibrillation.

A further object is to provide a waveform adapter for use with existing DSW defibrillators and other defibrillators designed to deliver a single type of waveform, whereby the energy from the existing defibrillator may be captured and converted to a different waveform, thus extending the useful life of existing defibrillators.

These and other objects and advantages of the present invention will become more apparent upon reading the following detailed description in conjunction with the accompanying drawings.

DETAILED DESCRIPTION OF THE PREFERRED EMBODIMENT

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In its preferred embodiment, the defibrillator 10 according to the present invention preferably operates solely with energy provided from the discharge of a DSW defibrillator, although an internal power source may be included if desired. The device 10 includes a pair of conducting pads on its exterior where the external defibrillator paddles can be placed so that the energy from the discharge is transferred to defibrillator 10, which then converts the energy to an arbitrary waveform. The device thereby acts as a waveform adapter for use with existing DSW defibrillators and other defibrillators designed to deliver a single type of waveform, whereby the energy from the existing defibrillator may be captured and converted to a different waveform. In this manner, the useful life of existing defibrillators may be extended without modification.

Figure 1:
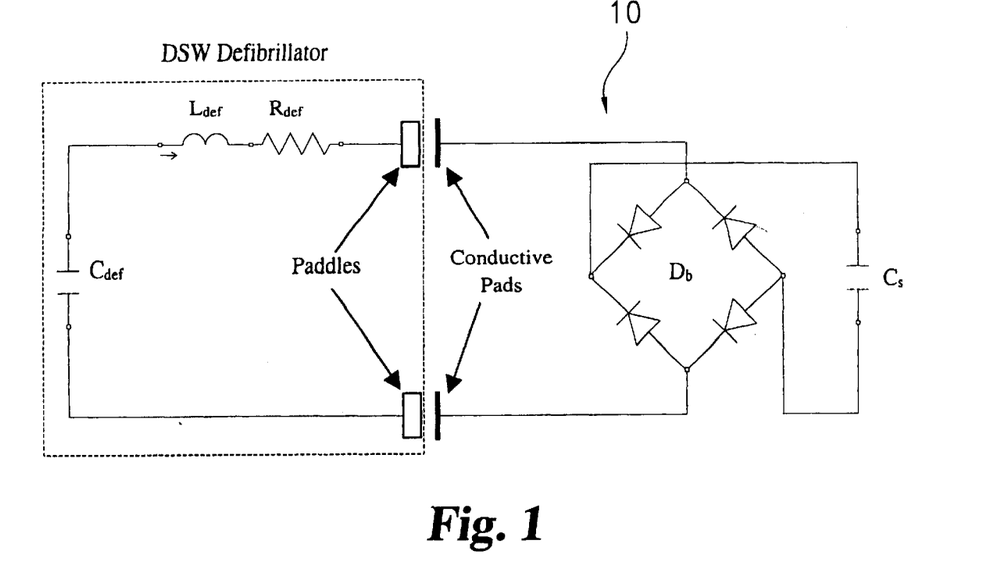
FIG. 1 is a schematic diagram of the energy transfer topology for the preferred embodiment of the present invention.

The method chosen to capture and convert this energy is to first store the energy in a capacitor and then use a step-down converter to deliver the energy in that capacitor in a controlled form to the load. As shown in FIG. 1, bridge rectifier $D_b$ connects the conducting pads to the storage capacitor $C_s$ so that paddle polarity is not important. In addition, if the DSW defibrillator waveform exhibits ringing, the energy in the negative phases can also be transferred to the storage capacitor with the bridge rectifier in place. When charged with an existing DSW defibrillator, defibrillator 10 is able to deliver a shock synchronized by the discharge of the DSW defibrillator and thus requires no additional ECG detecting hardware.

Because, in the preferred embodiment, the only energy available for delivering the arbitrary waveform is provided by a single DSW defibrillator, efficiency of the energy transfer is an important design parameter. Computer simulations of the circuit in FIG. 1 have been run to determine what value of $C_s$ would maximize energy transfer. With a 32-$\mu$F $C_{def}$, 36-mH $L_{def}$ and 10-$\Omega$ $R_{def}$ in the illustrated defibrillator model, a broad peak in the percentage of energy captured (70–75%) was found for values of $C_s$ between 20 and 40 $\mu$F. A device designed to maximize energy transfer from a DSW defibrillator would preferably use a storage capacitance in this range. The simulation indicated that the end voltage on $C_s$ would be 4500 volts at the completion of energy transfer from a $C_{def}$ initially charged up to 5200 volts. Accordingly, the step-down converter used to convert the energy on $C_s$ into an arbitrary waveform is rated for 4500 volts. A single K-film capacitor with such a rating may be used as the storage capacitor and a single converter may be used with a switching device capable of withstanding such voltage. However, the presently preferred switching device is an insulated gate bipolar transistor (IGBT). Since the IGBT breakdown voltage usually ranges between 1000 and 1500 volts, the converter preferably divides the voltage. Thus, the design allows for use of 1000 volt rated devices in an energy converter that is rated for a total voltage of 4500 volts to maximize energy capture efficiency.

Figure 2:
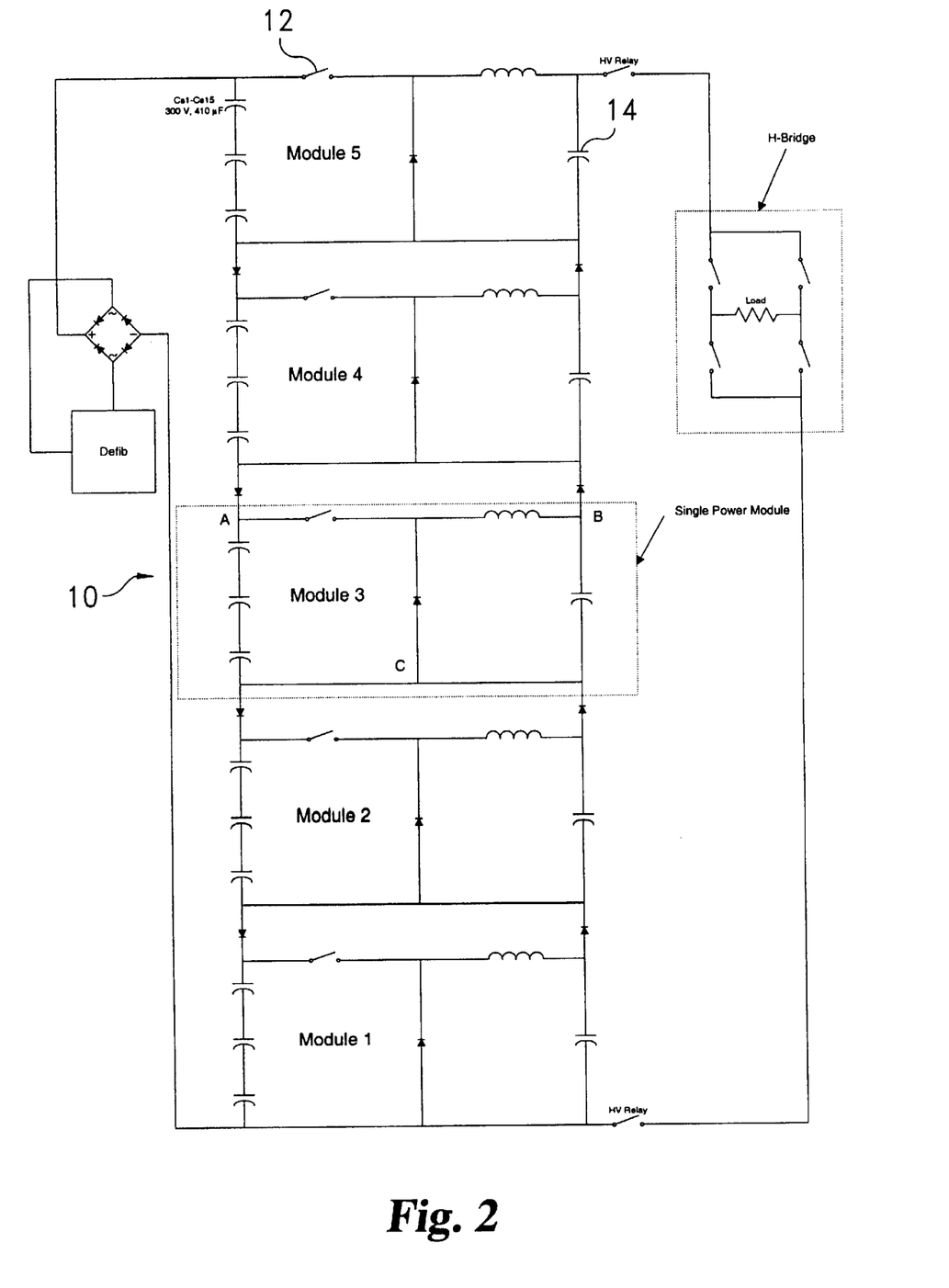
FIG. 2 is a schematic diagram of the preferred embodiment of a defibrillation waveform converter according to the present invention, shown connected to a conventional defibrillator as in FIG. I and also connected to a load.

Referring to FIG. 2, defibrillator 10 preferably includes a switching power converter comprising a series stack of 5 step-down converters, labeled as modules 1 through 5 in the drawing, each having a switch 12 which is preferably an insulated gate bipolar transistor (IGBT) or a parallel pair thereof, as will be described. The converter divides the 4500 volts stored by $C_s$ to 900 volts per module. The stack of storage capacitors at the left of the drawing comprises $C_s$ from FIG. 1 and is charged via the damped sine wave defibrillation discharge. As will be described, each module has an overvoltage shunt which prevents the input capacitors in the module from overcharging. Diodes in series with the stack of input capacitors prevent discharge of the stack in series. Each capacitor can only be discharged by its respective power converter. On the output side of the converters, there is another stack of output filtering capacitors 14. In their configuration with series diodes, each capacitor can only be charged up by the individual modules. On discharge into the load, the capacitors combine in series. Thus energy capture from the damped sine wave defibrillator occurs in series, energy conversion via the power converters occurs in parallel and discharge to the patient occurs in series.

The power converters used are step-down or buck converters. A limitation of the step-down converter is that the output voltage of the converter must be less than the input voltage and that the input and output voltages must have the same polarity. In order to deliver bidirectional waveforms, an H-bridge connects the patient or load resistance to the stack of output capacitors. The H-bridge allows for reversal of polarity of the load connection. To protect the H-bridge from potential overvoltage during the damped sine wave defibrillator discharge, high voltage relays are placed in series with the output capacitors and the H-bridge. The relays are open during the DSW discharge and closed once it is complete.

Figure 3:
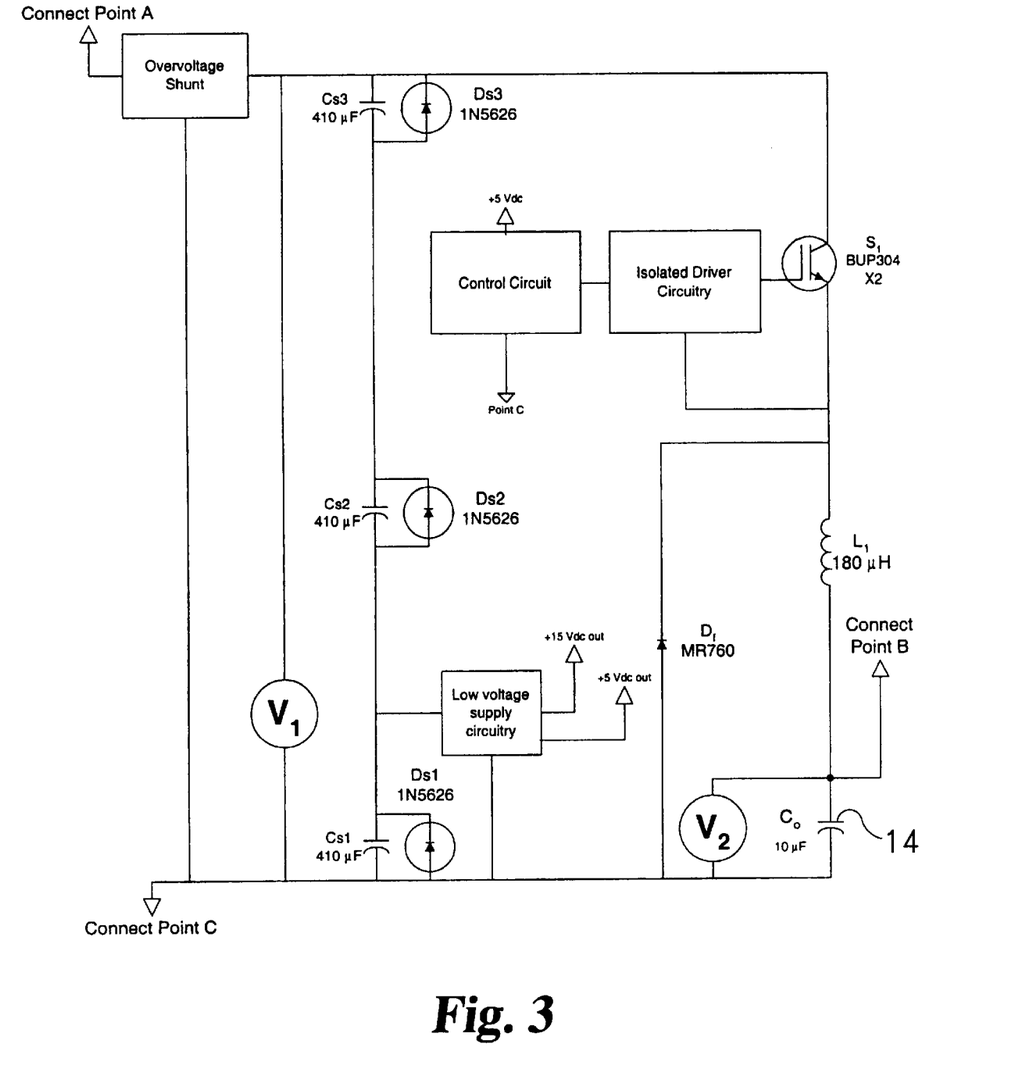
FIG. 3 is a schematic diagram of a power converter module in the waveform converter of FIG. 2.

Shown in FIG. 3 is a representation of a single power converter module. Note the three connection points labeled on the circuit (A, B, C) corresponding to the connection points of FIG. 2. Each module preferably contains three 300 volt, 410 $\mu$F capacitors (Cs1–Cs3) placed in series to give a maximum storage voltage of 900 volts. Diodes Ds1–Ds3 (1N5626) placed at the terminals of each storage capacitor prevent development of a negative voltage across the terminals during discharge. Alternatively, a single capacitor may be used. An overvoltage shunt circuit, described in further detail below, bypasses charging current around the module when the storage capacitance charges to 900 volts.

During operation, switch $S_1$, preferably a parallel pair of insulated gate bipolar transistors (IGBT's), cycles between the on and off states. During the on state, current in inductor $L_1$ ramps up and capacitor $C_o$ begins to charge. When $S_1$ is turned off, the flyback diode $D_f$, continues to conduct the current through $L_1$ and $C_o$. Control of waveforms appearing at output capacitor 14 ($C_o$) is achieved by adjusting the duty cycle of IGBT group $S_1$ (the percentage of time that the IGBT's are on during each switching cycle).

Figure 4:
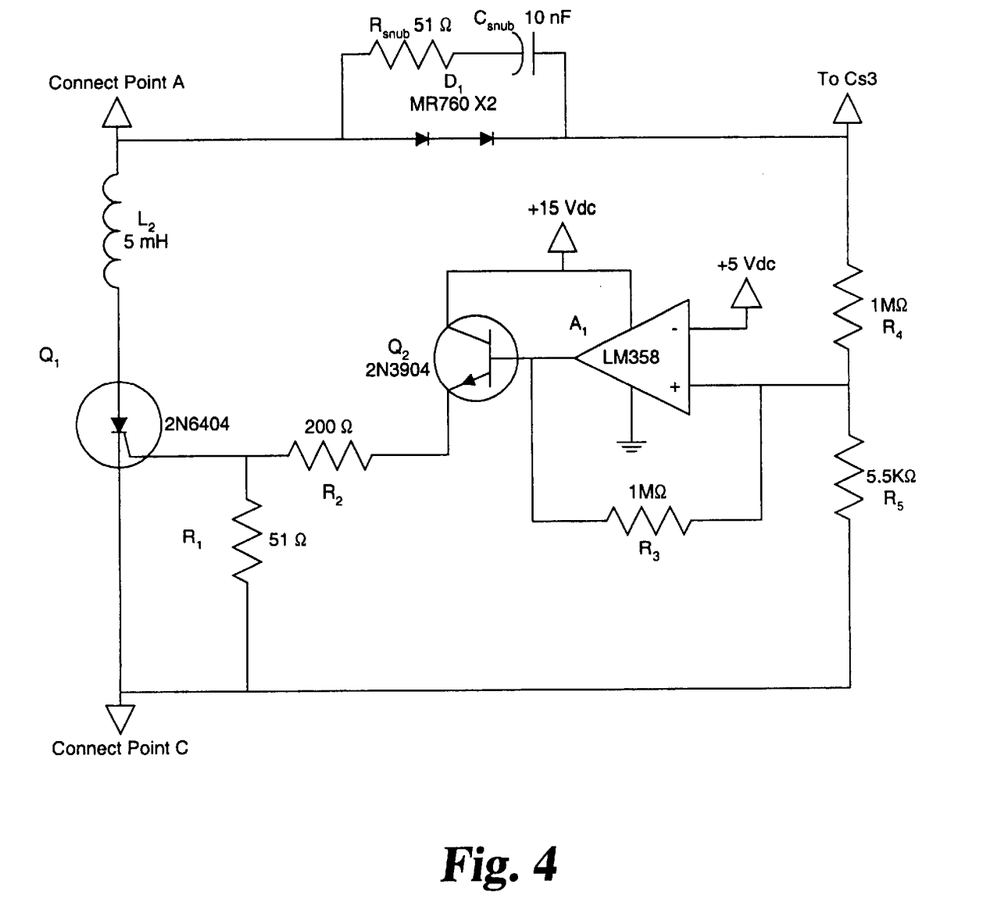
FIG. 4 is a schematic diagram of the overvoltage shunt circuitry in the power converter module of FIG. 3.

FIG. 4 shows a schematic of the overvoltage shunt circuitry present on each power module. Using an op-amp comparator, which may be an LM 358, the circuit detects when the voltage on the module storage capacitor reaches 900 volts. At this time, SCR $Q_1$ is activated creating a bypass for current around the power module. Diode $D_1$ prevents the now conducting SCR from discharging the storage capacitors. Two diodes are used in series to prevent exceeding the MR 760 diode voltage rating of 1000 volts. A snubber network is placed across the diodes to reduce voltage transients. Inductor $L_2$ limits inrush of current into the SCR when it is activated, preventing violation of its di/dt rating.

Figure 5:
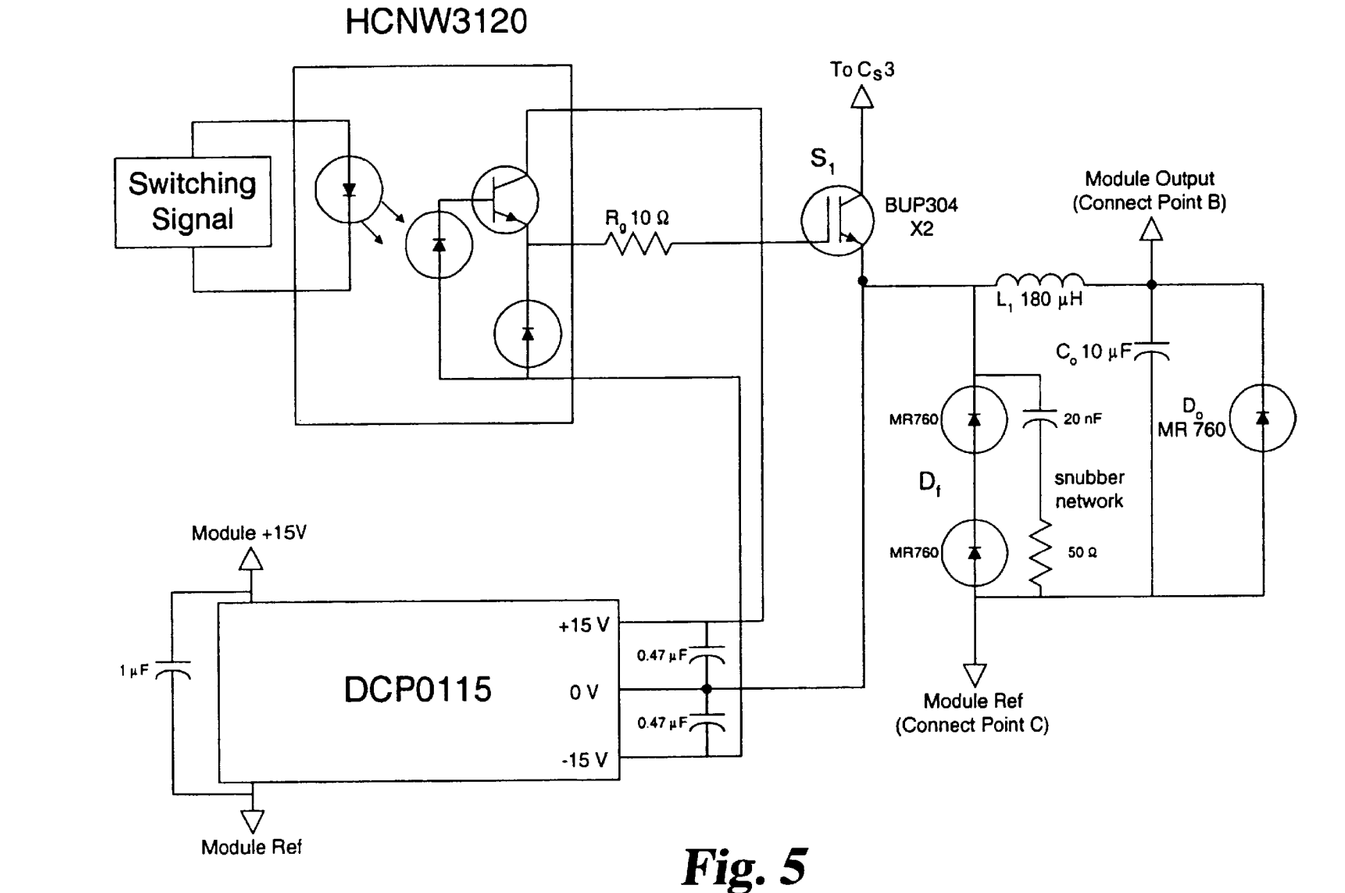
FIG. 5 is a schematic diagram of the isolated driver circuitry in the power converter module of FIG. 3.

FIG. 5 shows a schematic of the isolated driver circuitry of FIG. 3. In the circuit topology shown in FIG. 3, the gate and source of $S_1$ are floating above the module reference point. Thus, the drive circuitry for the IGBT's must be isolated from the module reference. As shown in FIG. 5, isolation of the switching signal, which is provided by the control circuit shown in block form in FIG. 3 and in detail in FIG. 7 described below, is accomplished by using a Hewlett Packard HCNW3120 IGBT gate driver integrated circuit. The output of the circuit is fed through a 10-$\Omega$ gate resistor to the gate of the IGBT. Isolation of the driver power supply is provided by a Burr Brown DCP0115 isolated ±15-volt supply. The DCP0115 is in turn powered by the module's low-voltage power supply discussed below with reference to FIG. 6. The gate driver is referenced to the −15-volt output while the IGBT source is referenced to the common terminal of the DCP0115. This places −15 volts on the gate in the off state, ensuring that the IGBT is not activated by spurious noise.

Also shown in FIG. 5 are further details of the step-down power converter of FIG. 3. The flyback diode $D_f$ is implemented using a pair of MR 760 diodes that are rated for 1000 volts each. The maximum steady state voltage that the diode pair should encounter is 900 volts, but due to parasitic inductances, transients occurring during the switching of $S_1$ could cause the reverse voltage on $D_f$ to exceed 1000 volts. Thus, two diodes are used in series. A snubber network is also placed across the diode pair to further guarantee they will not experience overvoltages. Finally, note a diode placed across the output capacitor of the converter. This diode, $D_o$, prevents the output capacitor from reverse charging and allows inactivated modules to pass current to the load.

As indicated above, the defibrillator waveform converter is preferably powered solely by external energy coming from the damped sine wave shock supplied by the external defibrillator. Low voltage supplies to power logic circuitry, op-amps and isolation devices thus derive power from the high voltage stored on each power converter module. A switching power converter allows for reduction of the high voltage present on the module storage capacitors without wasting much energy.

Figure 6:
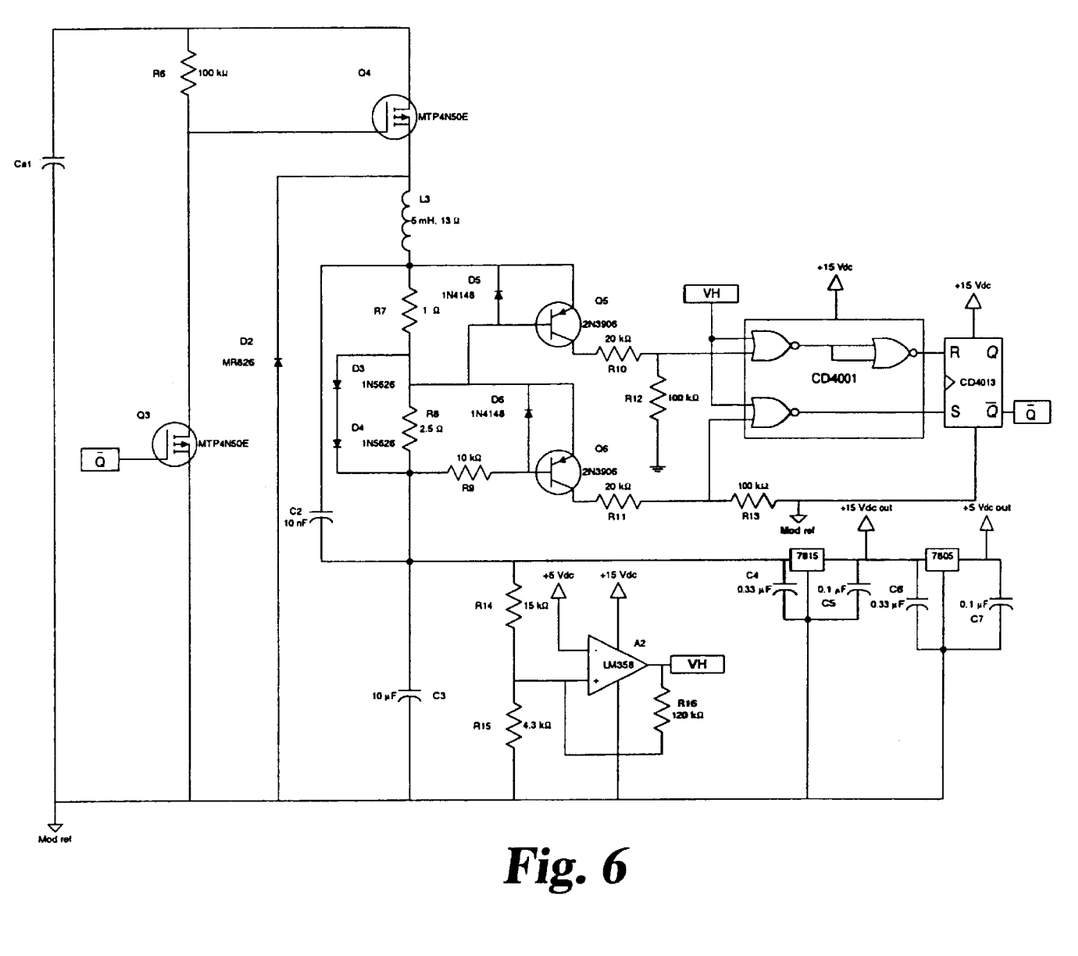
FIG. 6 is a schematic diagram of the power supply in the power converter module of FIG. 3.

FIG. 6 shows a suitable positive low-voltage power supply circuitry. Energy from the storage capacitor Cs1 is transferred to low voltage capacitor C3 using a step-down (buck) switch-mode DC-DC converter. MOSFET Q4 operates as the switching element and in the start-up conditions, initially is in the ON state. When ON, current increases through inductor L3. As current reaches 0.5 A, the voltage drop across R7 causes transistor Q5 to turn on. This sends a logic signal to the NOR gates and ultimately causes the flip-flop to reset. $\overline{Q}$ goes high and activates MOSFET Q3 which deactivates Q4. Current continues to flow through L3 and C3 via a new path created by diode D2. When this current decays to 0.25 A, the drop across R8 becomes low enough to turn off transistor Q6. This results in a set signal on the flip-flop that brings $\overline{Q}$ low and turns off Q3, turning on Q4. This sequence of events causes the current in L3 to ramp up and down between 0.25 and 0.5 amp. This continues to occur until the voltage across C3 reaches approximately 22 volts. At this time, op-amp A2, which is used as a comparator, outputs high. This causes a reset pulse at the flip-flop and inhibits set pulses. Resistor R16 provides about 2 volts of hysteresis on the comparator so that the voltage on C3 will have about 2 volts of ripple. A 7815 linear 15-volt regulator is used to generate a 15-volt source from the 20–22 volts present on C3. The 7805 generates a 5-volt source from the 15-volt source. Ripple is attenuated from the source by the linear regulators. The module 1 (bottom module) low voltage power supply is configured to ramp between current limits of 0.5 amp and 1 amp so that it has sufficient current to run the input voltage monitoring and relay control circuitry as well as the H-bridge circuitry.

When interconnected as in FIG. 2, the voltage on the entire stack of storage capacitors (Cs1–Cs15) cannot be directly measured because current cannot flow out of the stack in series when the series diodes are reverse biased. Thus, the storage capacitor voltage needs to be measured individually at each module, isolated and then summed. The high-voltage relays are triggered once the sum of the voltages of the storage capacitors reaches a threshold. The storage voltage on each module is measured from a voltage divider (not shown) on the storage capacitors. This voltage may isolated on each module via isolation circuitry of the type shown below in FIG. 7 including an HCPL-7820 isolation amplifier.

Knowledge of the voltage of the storage capacitors is important in generating a controlled-power output waveform, as will be discussed below. A voltage measurement on a storage capacitor during delivery of a waveform can have a negative error due to the equivalent series resistance (ESR) of the capacitor and the high currents that are possible through the capacitor. The ESR of the 410-$\mu$F storage capacitors was determined by applying pulsed current measuring the corresponding instantaneous step change in voltage. Each capacitor has an ESR of approximately 100 m$\Omega$. To avoid the measurement error present when the capacitor is conducting large amounts of current, measurements on the storage capacitors should be made during zero current conditions or when the converter switch is off.

As indicated above, the power modules have an isolated digital input that controls whether the IGBT's are in the ON state or the OFF state. The present invention contemplates the control of this input such that the modules can deliver an arbitrary shaped waveform.

The waveform converter is preferably operable as a controlled-power source as opposed to a controlled voltage or current source, although the latter modes of operation are contemplated as alternatives. Power to the load may be controlled by monitoring output current times output voltage and using the product as a feedback variable. Alternatively, and in the preferred embodiment, the voltage on the energy storage capacitors is monitored and used as a feedback variable. By controlling the rate at which the voltage on the energy storage capacitor ($C_s$ in FIGS. 1 and 2) decays, the rate of energy discharge and thus delivered power is controlled.

A relationship representing the decay of the voltage on $C_s$ is derived in order to deliver a waveform specified by its power envelope. The following is a derivation of the desired voltage decay on the energy storage capacitor to generate a rectangular waveform. Given that a rectangular waveform corresponds to constant power output, the energy delivered to the load may be expressed simply as the product of power and time, i.e., $U_{del}(t)=Pt$. The energy stored in the storage capacitor as a function of time is thus $$U_{Cs}(t) = U_i - \frac{Pt}{\varepsilon} \qquad (1)$$

where $U_i$ is the initial energy stored in the capacitor and $\epsilon$ is the power converter efficiency. Rewriting $U_{Cs}(t)$ in terms of the voltage on the capacitor gives $$1/2CV_{Cs}^2(t) = 1/2CV_{Ci}^2 - \frac{Pt}{\varepsilon} \qquad (2)$$

where C is the capacitance of capacitor $C_s$ and $V_{Ci}$ is the initial voltage on $C_s$. Solving for the storage capacitor voltage, $$V_{Cs}(t) = \sqrt{V_{Ci}^2 - \frac{2Pt}{C\varepsilon}} \qquad (3)$$

Figure 8:
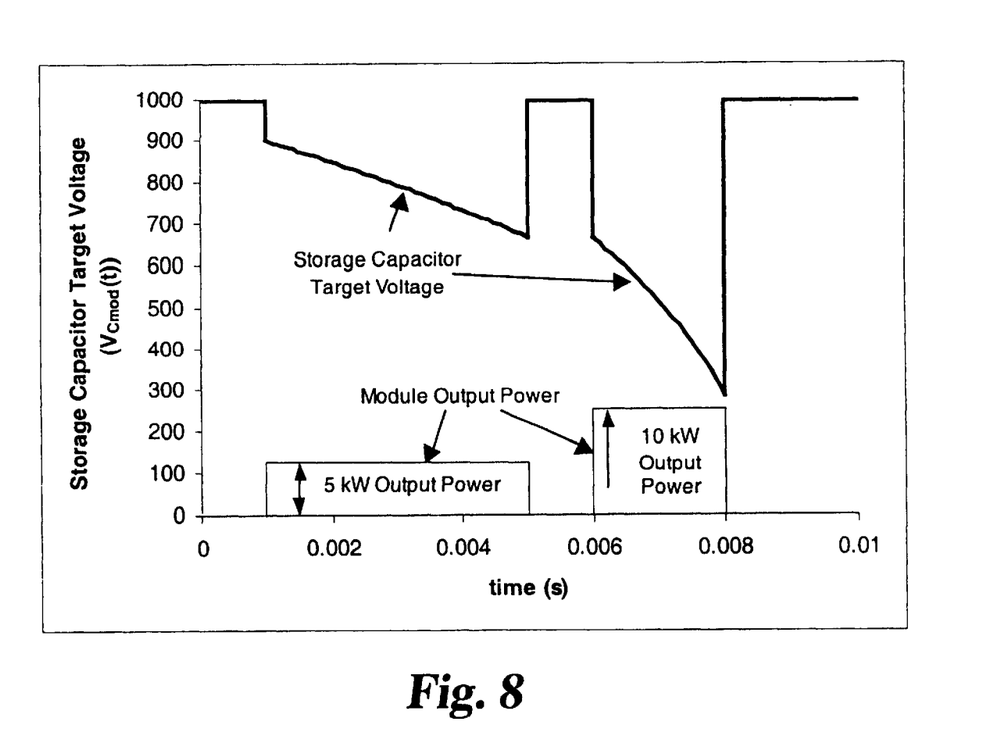
FIG. 8 is a plot of sample waveforms in accordance with the present invention.

A representative waveform according to this equation is shown in FIG. 8 above a corresponding rectangular power and voltage output to the patient. The initial voltage $V_{ci}$ is set at least as high as the voltage corresponding to the desired level of delivered energy according to the equation $$V = \sqrt{\frac{2U_{totdel}}{C}} \qquad (4)$$

The following is a derivation of the desired voltage decay on the energy storage capacitor to generate a waveform at the output with a truncated exponential power output. The monophasic truncated exponential defibrillation waveform can be written in terms of voltage as follows:

$$V(t)=V_i e^{-t/\tau} \qquad (5)$$

where $V_i$ is the initial voltage of the waveform, and $\tau$ is the time constant of decay. Similarly, the waveform can be expressed in terms of delivered power, assuming that the patient load is resistive and linear.

$$P(t)=P_i e^{-2t/\tau} \qquad (6)$$

where $P_i$ is the initial power delivered to the load. The energy delivered to the load is:

$$U_{del}(t) = P_i \int_0^t e^{-2\tilde{t}/\tau} d\tilde{t} = \frac{P_i \tau}{2}[1 - e^{-2t/\tau}] \quad (7)$$

The total energy delivered to the load for a waveform of duration d is:

$$U_{totdel} = P_i \int_0^d e^{-2t/\tau} dt = \frac{P_i \tau}{2}(1 - e^{-2d/\tau}) \quad (8)$$

Thus $P_i$ can be expressed as:

$$P_i = \frac{2U_{totdel}}{\tau(1 - e^{-2d/\tau})} \quad (9)$$

Combining 7 and 9 yields:

$$U_{del}(t) = U_{totdel} \frac{(1 - e^{-2t/\tau})}{(1 - e^{-2d/\tau})} \quad (10)$$

The energy remaining in $C_s$ during a discharge is expressed as:

$$U_{Cs}(t) = U_i - \frac{U_{del}(t)}{\varepsilon} = \frac{1}{2}CV_{Ci}^2 - \frac{U_{totdel}(1 - e^{-2t/\tau})}{\varepsilon(1 - e^{-2d/\tau})} \quad (11)$$

where $U_i$ is the initial energy stored in $C_s$, $V_{Ci}$ is the initial voltage on the capacitor $C_s$ and C is the capacitance of $C_s$. Rewriting $U_{Cs}(t)$ in terms of the voltage on $C_s$ gives:

$$\frac{1}{2}CV_{Cs}^2(t) = \frac{1}{2}CV_{Ci}^2 - \frac{U_{totdel}(1 - e^{-2t/\tau})}{\varepsilon(1 - e^{-2d/\tau})} \quad (12)$$

The equation for the voltage decay on $C_s$ is thus:

$$V_{Cs}(t) = \sqrt{V_{Ci}^2 - \frac{2U_{totdel}(1 - e^{-2t/\tau})}{C \cdot \varepsilon(1 - e^{-2d/\tau})}} \quad (13)$$

As indicated above, the defibrillator waveform converter uses five identical power modules that each have their own controller. Thus, equation (13) must be appropriately adapted to 5 identical target voltages for each controller. An additional possibility is to operate the controller such that less than 5 modules are activated. This may be advantageous in situations where low delivered energies are required for defibrillation. Equation (13) can be rewritten to express a voltage sent to each of n controllers where n can range between 1 and 5 depending on the number of modules used. The result, $V_{Cmod}$, is:

$$V_{Cmod}(t) = \sqrt{(\tilde{V}_{Ci})^2 - \frac{2U_{totdel}(1 - e^{-2t/\tau})}{n \cdot C_{mod} \cdot \varepsilon(1 - e^{-2d/\tau})}} \quad (14)$$

where $C_{mod}$ is the storage capacitance of 1 module and $\tilde{V}_{Ci}$ is the storage capacitor voltage of a single module at the start of the waveform.

A signal generator, which may be implemented in a computer, a digital signal processor or the like, is used to generate a control signal according to equation (3) or equation (14), and the control signal is used as the basis for generating digital switching pulses for the power modules. It will be appreciated from the foregoing that the waveform converter may be programmed to generate an arbitrarily shaped waveform. The preferred scheme for controlling switching converters is to use a pulse width modulator. The target waveform is compared to the delivered waveform and the width of each switching pulse is modulated so that the error between the two is minimized. The pulse width modulator typically delivers each of these modulated pulses at a fixed frequency. Such a modulator may be suitable for some applications of the present invention.

Figure 7:
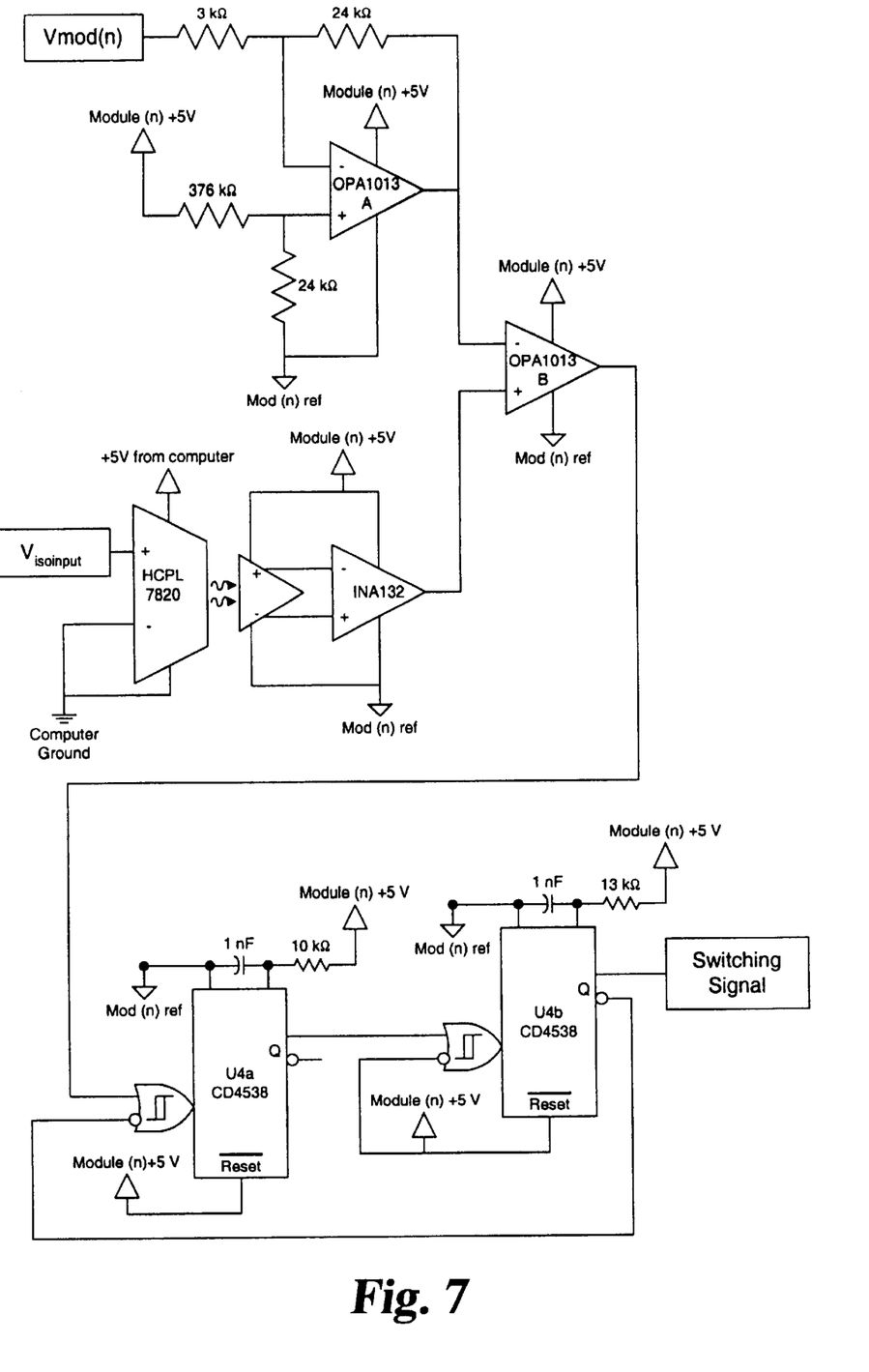
FIG. 7 is a schematic diagram of the control circuit in the power converter module of FIG. 3.

However, the method preferred for use with the defibrillator waveform converter uses a fixed pulse width and modulated spacing between pulses. Thus, the controller adjusts both the switching frequency and the duty cycle. Implementation of this method is shown in FIG. 7, in which $V_{mod}$ corresponds to actual module voltage and $V_{isoinput}$ corresponds to desired voltage as will be described. The modulation scheme works by comparing the target waveform of equation (14) with the voltage on the storage capacitors. If the voltage on the storage capacitors is larger, then $S_1$ is activated for a 10-μs pulse. The controller then waits an additional 3 μs before allowing an additional 10-μs pulse if the storage capacitor voltage still is greater than the target waveform. The 3-μs delay masks the effect of switching noise on the decision to initiate an additional 10-μs pulse. Thus, the controller switches the power module as needed to force a match between the voltage on the storage capacitors and equation (14). FIG. 7 shows a hardware implementation of the comparison and PWM pulse generation functions, but such functions may alternatively be implemented in a digital signal processor or in software under control of a microprocessor or other form of computer operating in conjunction with an analog-to-digital converter for conversion of the actual capacitor voltage. The waveform of equation (14) is scaled, isolated with HCPL-7820 isolation amplifiers and sent to each power module. Each power module begins with a starting storage capacitor voltage of 900 volts. Desired voltage $V_{Cmod}(t)$ also will need to start out at 900 volts or above to prevent the module from delivering power prematurely. When the output waveform is desired, $V_{Cmod}$ will drop down to 900 volts and then decay according to equation (14). During a condition when zero output power is required such as during the separation time between phases of a bidirectional waveform or at the end of a waveform, $V_{Cmod}$ will then rise back above the voltage on the storage capacitors to prevent the controller from switching.

To make the device safe in the event that the signal generator becomes disconnected from the waveform converter, it is desirable to have a zero-volt waveform converter input correspond to zero power output. To be fed into a HCPL-7820 isolation amplifier, $V_{Cmod}(t)$ is scaled, inverted and summed with a constant as follows:

$$V_{isoinput}(t) = 0.3 - 0.0003 \cdot V_{Cmod}(t) \quad (15)$$

Likewise the module storage capacitor voltage is also inverted and summed with a constant. The comparator is then set up to activate $S_1$ for a 10-μs pulse when $V_{Cmod}$ exceeds the storage capacitor voltage. If for some reason the signal generator is not on or is disconnected, the module storage capacitor voltage will never exceed $V_{Cmod}$ and no power will be delivered.

As the waveform converter has an output H-bridge, the capability exists to deliver waveforms that are bi-directional. H-bridge operation requires that there is a 400-μs delay between the end of phase 1 and the start of phase 2. Thus, the power converters should be off at this time. In order to accomplish this, $V_{Cmod}(t)$ is simply brought to a voltage guaranteed to be higher than the storage capacitor voltage can ever be. When the next phase starts, $V_{Cmod}(t)$ returns to its final value at the end of the previous phase, as shown in FIG. 8. In this figure, $V_{Cmod}(t)$ is placed at 1000 volts when zero power out is needed in the waveform.

FIG. 8 illustrates a sample waveform for the storage capacitor target voltage and the corresponding module output waveform, which is a rectangular voltage (and power) waveform and is a preferred waveform for use with the present invention. A rectangular waveform is preferred as this waveform can be mathematically shown to deliver the maximal amount of average current for a given amount of delivered energy (see following paragraph). The waveform is preferably a biphasic, bidirectional waveform, with equal-amplitude first and second phases. The duration is preferably equal to the chronaxie of the heart for optimum efficiency. The ratio of charge delivered in the second phase to charge delivered in the first phase ($Q_2/Q_1$) is preferably in the range of 0.2–0.7, and more preferably in the range of 0.3–0.4. As a particular example of a preferred waveform of this type, the waveform may have a 4-ms phase 1 duration and a 1.5-ms phase 2 duration, which yields a Q2/Q1 of 0.375.

The energy delivered with a rectangular pulse of average current $\bar{I}$ into load resistance R is:

$$U_R = \bar{I}^2 R d \tag{16}$$

Any arbitrary pulse of current i(t) can be represented as a sum of the average current of the waveform and remaining zero-average current component $i_r(t)$:

$$i(t) = \bar{I} + i_r(t) \tag{17}$$

where:

$$\bar{I} = \frac{1}{d} \int_0^d i(t) dt \tag{18}$$

Because the remaining term must have zero average current then:

$$\int_0^d i_r(t) dt = 0 \tag{19}$$

The energy delivered by this arbitrary waveform is:

$$U = \int_0^d i^2(t) R dt = R \int_0^d (\bar{I}^2 + 2\bar{I} \cdot i_r(t) + i_r^2(t)) dt \tag{20}$$
$$= R\bar{I}^2 \int_0^d dt + 2R\bar{I} \int_0^d i_r(t) dt + R \int_0^d i_r^2(t) dt$$

Note that the first term on the right-hand side of equation (20) is equal to $U_R$ and the second term is zero according to equation (19). Thus, for this arbitrary waveform to be equally or more efficient than a rectangular waveform, the third term must be $\leq 0$. The only case in which this is true is when $i_r$ is equal to zero and this is the case in which the arbitrary waveform is also rectangular.

Therefore, the rectangular waveform requires the least amount of delivered energy to achieve a fixed average current. According to the average-current model for defibrillation, this waveform is the most efficacious for a given amount of delivered energy.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, the power converter may use a boost or buck-boost topology if an output voltage greater than the input voltage is desired.

We claim:

1. A controlled-power defibrillator for automatically compensating for changes in patient resistance during delivery of a defibrillation pulse, comprising:
   an energy storage device;
   a pair of electrodes adapted for connection to a patient's body;
   a power converter having an input connected to said energy storage device and an output connected to said electrodes; and
   a closed-loop power control circuit operatively connected to said power converter for controlling the power delivered to the patient, said power control circuit including means for generating a control signal having a defined relationship with a desired delivered power waveform, means for monitoring a parameter having a defined relationship with actual delivered power, and means for adjusting the delivery of power to the patient as a function of the difference between desired power and actual power.

2. The controlled-power defibrillator of claim 1, wherein said monitored parameter is an electrical parameter of said energy storage device.

3. The controlled-power defibrillator of claim 2, wherein said monitored parameter is an electrical parameter other than power.

4. The controlled-power defibrillator of claim 3, wherein said energy storage device is a storage capacitor and said monitored parameter is the voltage on said storage capacitor during delivery of the defibrillation pulse.

5. The controlled-power defibrillator of claim 4, wherein said power converter is a switching power converter including an electronic switch, and wherein said means for adjusting the delivery of power has an output connected to said switch.

6. The controlled-power defibrillator of claim 5, wherein said means for generating a control signal includes means for generating an arbitrary waveform.

7. The controlled-power defibrillator of claim 6, wherein said means for generating a control signal includes means for generating a storage capacitor voltage signal corresponding to a rectangular defibrillation waveform.

8. The controlled-power defibrillator of claim 7, wherein said switching power converter includes a plurality of power converter modules each including an electronic switch controlled by said means for adjusting the delivery of power, said power converter modules having outputs connected in series for series discharge into the patient.

9. A waveform adapter for use with an existing defibrillator capable of generating a first waveform, comprising:
   means for capturing energy from the discharge of said defibrillator;
   a pair of electrodes adapted for connection to a patient's body;
   a power converter having an input connected to said means for capturing energy and an output connected to said electrodes, said power converter including means for converting captured energy from the existing defibrillator to a second waveform.

10. The waveform adapter of claim 9, wherein said means for capturing energy includes a bank of energy storage devices connected in series, and wherein said power converter includes a plurality of power converter modules with inputs connected to respective energy storage devices in said bank and with outputs connected in series, whereby energy can be captured from said existing defibrillator in series, converted to said second waveform in parallel and redelivered to the patient in series.

11. The waveform adapter of claim 10, wherein said means for capturing energy further includes a pair of conductive pads adapted for connection to output electrodes of the existing defibrillator, and a rectifier connected between said pads and said bank of energy storage devices.

12. The waveform adapter of claim 11, wherein said waveform adapter is powered solely by captured energy from the existing defibrillator.

13. A controlled-power method of defibrillation with automatic compensation for changes in patient resistance during delivery of a defibrillation pulse, comprising the steps:

storing energy in an energy storage device;

delivering energy from said energy storage device to a patient through a power converter; and controlling the power converter so as to control the power delivered to the patient, said controlling step including generating a control signal having a defined relationship with a desired delivered power waveform, monitoring a parameter having a defined relationship with actual delivered power, and adjusting the delivery of power to the patient as a function of the difference between desired power and actual power.

14. The method of claim 13, wherein said monitored parameter is an electrical parameter of said energy storage device.

15. The method of claim 14, wherein said monitored parameter is an electrical parameter other than power.

16. The method of claim 15, wherein said energy storage device is a storage capacitor and said monitored parameter is the voltage on said storage capacitor during delivery of the defibrillation pulse.

17. The method of claim 16, wherein said power converter is a switching power converter including an electronic switch, and wherein said adjusting step includes controlling said switch.

18. The method of claim 17, wherein said signal generating step is performed with means for generating an arbitrary waveform.

19. The method of claim 18, wherein said signal generating step includes generating a storage capacitor voltage signal corresponding to a rectangular defibrillation waveform.

20. The method of claim 19, wherein said switching power converter includes a plurality of power converter modules each including an electronic switch controlled in said adjusting step, and wherein said power converter modules have outputs connected in series for series discharge into the patient.

21. A method of adapting an existing defibrillator for use with a different waveform, comprising the steps:

capturing energy delivered in one form from the discharge of the existing defibrillator;

converting captured energy from the existing defibrillator to another form; and delivering converted energy to a patient.

22. The method of claim 21, wherein said capturing step is performed with a bank of energy storage devices connected in series, and wherein said converting step is performed with a plurality of power converter modules with inputs connected to respective energy storage devices in said bank and with outputs connected in series, whereby energy can be captured from said existing defibrillator in series, converted to said another form in parallel and redelivered to the patient in series.

23. The method of claim 22, wherein said capturing step includes connecting a pair of conductive pads to output electrodes of the existing defibrillator and rectifying the signal received from said existing defibrillator.

24. The method of claim 23, wherein said method is performed with circuitry powered solely by captured energy from the existing defibrillator.

* * * * *

UNITED STATES PATENT AND TRADEMARK OFFICE
CERTIFICATE OF CORRECTION

PATENT NO.     : 6,546,287 B1
DATED          : April 8, 2003
INVENTOR(S)    : William J. Havel et al.

It is certified that error appears in the above-identified patent and that said Letters Patent is hereby corrected as shown below:

<u>Column 11,</u>
Line 43, please delete "9" at the end of equation (18)

Signed and Sealed this

Sixteenth Day of September, 2003

JAMES E. ROGAN
*Director of the United States Patent and Trademark Office*